United States Patent
Ura et al.

(10) Patent No.: US 6,197,728 B1
(45) Date of Patent: *Mar. 6, 2001

(54) QUINOXALINE DERIVATIVES AND HERBICIDAL COMPOSITION

(75) Inventors: Yasukazu Ura; Gozyo Sakata; Kenzi Makino; Yasuo Kawamura, all of Funabashi; Yūzi Kawamura, Shiraoka-machi; Takasi Ikai, Shiraoka-machi; Tosihiko Oguti, Shiraoka-machi, all of (JP)

(73) Assignee: Nissan Chemical Industries Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 08/297,758

(22) Filed: Aug. 30, 1994

Related U.S. Application Data

(62) Division of application No. 06/175,706, filed on Aug. 6, 1980, now Pat. No. 5,364,831.
(51) Int. Cl.$^7$ .................................................. A01N 43/60
(52) U.S. Cl. .......................................................... 504/235
(58) Field of Search ............................................ 504/235

(56) References Cited

U.S. PATENT DOCUMENTS

| | | | |
|---|---|---|---|
| 4,609,396 | * | 9/1986 | Fawzi .................................... 504/235 |
| 4,629,493 | | 12/1986 | Ura et al. ............................. 544/354 |
| 5,364,831 | * | 11/1994 | Ura et al. ............................. 504/235 |

\* cited by examiner

*Primary Examiner*—Bernard Dentz
(74) *Attorney, Agent, or Firm*—Oblon, Spivak, McClelland, Maier & Neustadt, P.C.

(57) ABSTRACT

Quinoxaline derivatives having the formula I

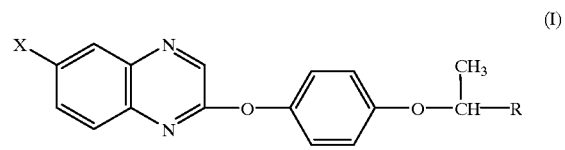

wherein X represents a halogen atom; R represents —COR$^1$,

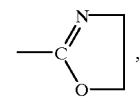

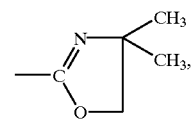

—CH=CH—COOR$^2$ (R$^2$ represents a C$_1$–C$_4$ alkyl group); —CN or —CH$_2$OH, and R$^1$ represents

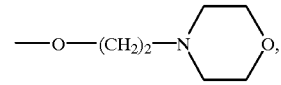

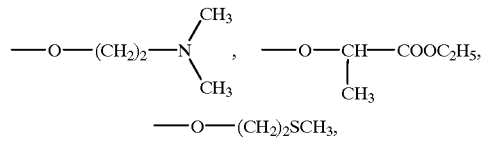

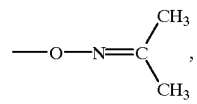

—S—R$^3$ (R$^3$ represents a C$_1$–C$_4$ alkyl or alkenyl group or phenyl or chlorophenyl group), —NH—R$^4$ (R$^4$ represents a C$_1$–C$_4$ alkoxy carbonylalkyl group, hydroxy alkyl group, phenyl group, C$_1$–C$_4$ alkoxy alkyl group or di C$_1$–C$_4$ alkyl amino group) are remarkably effective as selective herbicides.

7 Claims, No Drawings

QUINOXALINE DERIVATIVES AND HERBICIDAL COMPOSITION

This is a division of application Ser. No. 06/175,706, filed on Aug. 6, 1980 now U.S. Pat. No. 5,364,831.

BACKGROUND OF THE INVENTION

1. Field of the Invention

The present invention relates to novel quinoxaline derivatives and herbicidal compositions containing the same.

2. Decsription of the Prior Arts

Various compounds have been practically used as herbicides as a result of various studies on herbicides for long years. These herbicides have been proposed and practically used to contribute for elimination of agricultural labour works and to improve productivities of agricultural and horticultural crop plants.

It has been still awaited to find novel herbicides having superior herbicidal characteristics. The herbicides for agricultural and horticultural purposes are preferably compounds which selectively control the object weeds at a small dose without a toxicity to the crop plants. The known herbicides do not always have the optimum herbicidal characteristics.

The inventors have studied to develop novel useful herbicides especially on herbicidal characteristics of various heterocyclic compounds.

Substituted pyridyloxyphenoxy fatty acid herbicides have been known as heterocyclic ether type phenoxy fatty acid derivatives in Japan Unexamined Patent Publication No. 106735/1976.

Benzimidazole, benzthiazole, and benzoxazole derivatives and herbicidal effect of these compounds have been known in Japanese Unexamined Patent Publication No. 40767/1978.

SUMMARY OF THE INVENTION

It is an object of the present invention to provide novel quinoxaline derivatives.

It is another objects of the present invention to provide a herbicidal composition which has excellent selective herbicidal activity to various weeds especially gramineous weeds but substantially non-phytotoxicity to broad leaf crop plants.

The foregoing and other objects of the present invention have been attained by providing novel compounds having the formula $$\text{(I)}$$

wherein X represents a halogen atom; R represents —COR$^1$,

—CH=CH—COOR$^2$ ($R^2$ represents a $C_1$–$C_4$ alkyl group); —CN or —CH$_2$OH, and R$^1$ represents —S—R$^3$ ($R^3$ represents a $C_1$–$C_4$ alkyl or alkenyl group or phenyl or chlorophenyl group), —NH—R$^4$ ($R^4$ represents a $C_1$–$C_4$ alkoxy carbonylalkyl group, hydroxy alkyl group, phenyl group, $C_1$–$C_4$ alkoxy alkyl group or di $C_1$–$C_4$ alkyl amino group).

The present invention provides also herbicidal compositions comprising the novel quinoxaline derivative as an active ingredient.

DETAILED DESCRIPTION OF THE PREFERRED EMBODIMENTS

The quinoxaline derivatives having the formula (I) of the present invention are the novel compounds.

The quinoxaline derivatives having the formula (I) of the present invention are significantly unique compounds which are effective for controlling gramineous weeds without any phytotoxicity to broad leaf crop plants as well as broad leaf weeds especially in a post-emergence treatment. Such unique characteristics have not found.

Typical compounds of the present invention having the formula (I) are shown in Table (1) together with the physical properties. The present invention are not limited to the typical compounds shown in Table 1.

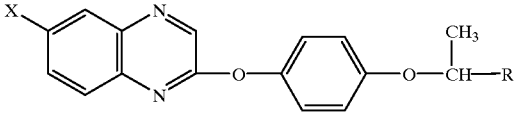

| Comp. No. | X | R | Physical Property | |
|---|---|---|---|---|
| 1 | F | —COO(CH₂)₂—N(morpholine) | $N_D^{22}$ = 1.4666 | Colorless liq. |
| 2 | " | —COO(CH₂)₂—N(CH₃)₂ | mp 69–71° C. | W.C. |
| 3 | " | —COOCH(CH₃)COOC₂H₅ | $N_D^{22}$ = 1.5513 | Colorless liq. |
| 4 | " | —COS CH₃ | mp 111–113° C. | W.C. |
| 5 | " | —CONHCH₂COOC₂H₅ | mp 143–145° C. | W.C. |
| 6 | " | —CONHCH₂CH₂OH | | W.C. |
| 7 | " | —C(=N)—O— (oxazoline) | mp 159–161° C. | W.C. |
| 8 | " | —C(=N)—O—C(CH₃)₂ (dimethyloxazoline) | mp 95–97° C. | W.C. |
| 9 | " | —CH=CH—COOCH₃ | mp 92–94° C. | W.C. |
| 10 | " | —CN | mp 104–105° C. | W.C. |
| 11 | " | —CH₂OH | mp 93–94° C. | W.C. |
| 12 | Cl | —COO(CH₂)₂SCH₃ | | Colorless liq. |
| 13 | " | —COON=C(CH₃)₂ | mp 128–130° C. | W.C. |
| 14 | " | —COSCH₃ | mp 109–110° C. | W.C. |
| 15 | " | —COSC₂H₅ | mp 92–93° C. | W.C. |
| 16 | " | —COSCH₂CH=CH₂ | mp 103–104° C. | W.C. |
| 17 | " | —COS—C₆H₅ | $N_D^{22}$ = 1.6390 | Colorless liq. |
| 18 | " | —COS—C₆H₄—Cl | mp 107–108° C. | W.C. |
| 19 | " | —CONH—C₆H₅ | mp 130–132° C. | W.C. |
| 20 | " | —CONHCH₂CH₂OCH₃ | mp 134–135° C. | W.C. |
| 21 | " | —CONHN(CH₃)₂ | mp 182–183° C. | W.C. |
| 22 | Cl | —C(=N)—O— (oxazoline) | mp 173–174° C. | W.C. |
| 23 | " | —CH=CHCOOCH₃ | $N_D^{20}$ = 1.5421 | Colorless liq. |
| 24 | " | —CH=CHCOOC₂H₅ | $N_D^{\circ}$ = 1.5630 | Colorless liq. |
| 25 | " | —CN | mp 125–126° C. | W.C. |
| 26 | " | —CH₂OH | | Colorless liq. |
| 27 | Br | —CH=CHCOOCH₃ | $N_D^{20}$ = 1.5468 | Colorless liq. |
| 28 | " | —CH₂OH | $N_D^{20}$ = 1.5530 | Colorless liq. |
| 29 | " | —C(=N)—O— (oxazoline) | mp 143–145° C. | W.C. |

Note: W.C.: white crystal

The compound (I) of the present invention can be produced by the following processes.

A) The compound of the present invention can be produced by a condensation of a compound having the formula

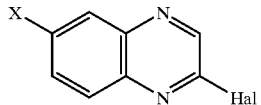

wherein X and Hal designate a halogen atom; with 4-hydroxyphenoxy derivative having the formula

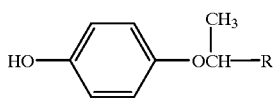

wherein R is defined above, in the presence of an inorganic or organic base such as sodium hydroxide, potassium hydroxide or potassium carbonate, at suitable temperature.

The reaction can be carried out in an inert solvent such as dimethylformamide, dimethylsulfoxide, or acetonitrile.

B) The compound of the present invention can be produced by a condensation of a compound having the formula (II) with a hydroquinone monobenzyl ether having the formula

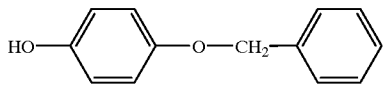

in the presence of an inorganic or organic base to produce a compound having the formula

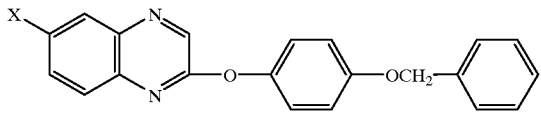

and then a hydrogenation of the product with a catalyst such as palladium-carbon catalyst to result a debenzylation and to obtain a compound having the formula

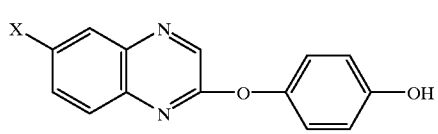

and then a condensation of the product with a faloakyl derivative having the formula

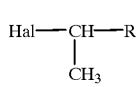

in the presence of an inorganic or organic base such potassium carbonate in a polar organic solvent such as methyl ethyl ketone, acetonitrile or dimethyl-formamide.

C) The product obtained by the process A) or B) is converted into the other compounds of the present invention by a hydrolysis, an esterification, an ester interchange, a salt or an amidation.

In the esterification, it is possible to use the conventional coupling agents as well as unique coupling agents such as imido coupling agents especially dicyclohexyl carboimide. The concentrations of the reagents and the temperatures in the reactions and kinds of the inert solvents can be selected as desired.

In the process A), the reaction is preferably carried out at 50 to 200° C. especially at 80 to 100° C., at a molar ratio of the compound (II): 4-hydroxyphenoxy derivative (III) of 1:0.2 to 5.0 preferably 1:0.5 to 2.0 especially 1:0.8 to 1.5. The inorganic or organic bases can be any base which is useful for the condensation of the compound (II) and the compound (III). The concentration of the starting materials in the inert solvent can be in a range of 5 to 50 wt. % preferably 10 to 30 wt. %.

In the process B), the reaction is preferably carried out at 50 to 200° C. especially at 100 to 150° C. at a molar ratio of a compound (II): a hydroquinone monobenzyl ether (IV) of 1:0.2 to 5.0 preferably 1:0.5 to 2.0 especially 1:0.8 to 1.5. The inorganic or organic base can be any base which is useful for the condensation of the compound (II) and the compound (IV). The reaction is preferably carried out in an inert solvent at a concentration of the starting material of 5 to 50 wt. % preferably 10 to 30 wt. %.

The hydrogenation of the resulting intermediate (V) is carried out in the condition for the debenzylation to obtain the compound (VI). The hydrogen pressure is preferably in the range of 1 to 5 atm. preferably 1 to 2 atm.

The reaction of the compound (VI) with the compound (VII) is preferably carried out at 80 to 100° C. at a molar ratio of the compound (VI): the compound (VII) of 1:0.2 to 5.0 preferably 1:0.5 to 2.0 especially 1:0.8 to 1.5. The inorganic or organic base can be the same ores. The concentration of the starting materials in the inert solvent can be in a range of 5 to 50 wt. % preferably 10 to 30 wt. %.

In the process C), the conditions of the hydrolysis, the esterification, the ester interchange, the neutralization and the amidation can be selected as desired. These conditions can be considered by a person skilled in the art.

Certain examples for the preparations of the present invention will be described.

Preparation 1

2-[1-{4-(6-fluoro-2-quinoxalyoxy)phenoxy}-ethyl]-4,4-dimethyl-2-oxazoline (Compound 8)

In 20 ml. of dimethyl-formamide, 2.0 g. (0.0070 mol) of 6-fluoro-2-(4-hydroxyphenoxy)-quinoxaline, 1.8 g. (0.0087 mol) of 2-(1-bromoethyl)-4,4-dimethyl-2-oxazoline and 1.3 g. (0.0094 mol) of potassium carbonate were dissolved and the mixture was heated at 90° C. for 8 hours to react them. After cooling, the reaction mixture was poured into water and the product was extracted with benzene. and the benzene layer was washed with 2% aqueous solution of sodium hydroxide and then with water and the benzene layer was dehydrated over sodium sulfate. The solvent was distilled off. The resulting crude crystal was washed with n-hexane to obtain 0.8 g (yield 27%) of the object compound.

Preparation 2

Methyl γ-methyl-γ-[4-(6-fluoro-2-quinoxalyloxy) phenoxy]crotonate (Compound 9)

In 150 ml. of methyl ethyl ketone, 2.6 g.(0.01 mol) of 6-fluoro-2-(4'-hydroxyphenoxy)quinoxaline, 2.0 g.(0.01 mol) of methyl γ-bromo-γ-methyl crotonate and 2.0 g.(0.014 mol) of potassium carbonate were dissolved and the mixture was refluxed for 8 hours.

After the reaction, the precipitate was separated by a filtration and the filtrate was concentrated and dried. The residue was dissolved in chloroform and the chloroform solution was washed with 5% aqueous solution of sodium hydroxide and then with water and, dehydrated, condensed and dried. The residual solid product was purified by a column chromatography with silica gel and chloroform to obtain 3.0 g. of white crystal of Compound No. 22 having a melting point of 92.0–94.0° C. (yield of 82%)

Preparation 3

2-[4-(6-fluoro-2-quinoxalyloxy)phenoxy]propanol (Compound 11)

In 50 ml. anhydrous ethyl ether, 0.5 g. (1.5 m mol) of methyl 2-[4-(6-fluoro-2-quinoxalyloxy)phenoxy]propionate was dissolved and 10 ml. of a solution containing 0.11 g.(3.0 mmol) of LiAlH$_4$ in anhydrous ethyl ether was added dropwise and the mixture was refluxed for 12 hours. After the reaction, 10 ml. of water and 7 ml. of 2N—H$_2$SO$_4$ were added to the reaction mixture and the organic layer was separated and washed with water and dehydrated over anhydrous sodium sulfate and the solvent was distilled off to obtain viscous liquid. This viscous liquid was crystallized and the crystal was washed with n-hexane to obtain 0.25 g. of the object compound (yield of 54%).

Preparation 4

2-[4-(6-chloro-2-quinoxalyloxy)phenoxy]propionic thioethyl ester (Compound 15)

In 50 ml. of tetrahydrofuran, 1.0 g.(2.90 mmol) of 2-[4-(6-chloro-2-quinoxalyloxy)phenoxy]propionic acid, 0.66 g.(3.2 mmol) of N,N-dicyclohexyl carbodiimide, 0.43 g. (3.2 mmol) of 1-hydroxy-benzotriazole and 0.32 g.(3.2 mmol) of triethylamine were dissolved. Into the solution, 0.20 g.(3.2 mmol) of ethyl mercaptane was added and the mixture was stirred at the ambient temperature for 24 hours. After the reaction, N, N-dicyclohexyl urea was separated by a filtration and tetrahydrofuran was distilled off under a reduced pressure and a residue was dissolved in chloroform. The chloroform layer was washed with an aqueous solution of sodium bicarbonate and then, dehydrated over anhydrous sodium sulfate and concentrated and dried to obtain 1.1 g. of a crude product. The crude product was purified by a silica chromatography with chloroform to obtain 0.45 g. of white crystal of the object compound having a melting point of 92 to 93° C. (yield of 40%)

The compound of the present invention can be used as a herbicidal composition.

In the preparation of the herbicidal compositions, the compound of the present invention can be uniformly mixed with or dissolved in suitable adjuvants such as solid carrier such as clay, talc, bentonite, diatomaceous earth; liquid carrier such as water, alcohols (methanol, ethanol etc.), aromatic hydrocarbons (benzene, toluene, xylene etc.) chlorinated hydrocarbons, ethers, ketones, esters (ethyl acetate etc.), acid amides (dimethylformamide etc.) if desired, with an emulsifier, a dispersing agent, a suspending agent, a wetting agent, a spreader, or a stabilizer to form a solution, an emulsifiable concentrate, a wettable powder, a dust, a granule or a flowable suspension which is applied if desired, by diluting it with suitable diluent.

It is possible to combine the compound of the present invention with the other herbicide, or an insecticide, a fungicide, a plant growth regulator, a synergism agent.

Certain examples of the herbicidal compositions of the present invention will be illustrated. In the examples, the part means part by weight.

Solution

Active ingredient: 5 to 75 wt. % preferably 10 to 50 wt. % especially 15 to 40 wt. %

Solvent: 95 to 25 wt. % preferably 88 to 30 wt. % especially 82 to 40 wt. %

Surfactant: 1 to 30 wt. % preferably 2 to 20 wt. %

Emulsifiable Concentrate

Active ingredient: 2.5 to 50 wt. % preferably 5 to 45 wt. % especially 10 to 40 wt. %

Surfactant: 1 to 30 wt. % preferably 2 to 25 wt. % especially 3 to 20 wt. %

Liquid carrier: 20 to 95 wt. % preferably 30 to 93 wt. % especially 57 to 85 wt. %

Dust

Active ingredient: 0.5 to 10 wt. %

Solid carrier: 99.5 to 90 wt. %

Flowable Suspension

Active ingredient: 5 to 75 wt. % preferably 10 to 50 wt. %

Water: 94 to 25 wt. % preferably 90 to 30 wt. %

Surfactant: 1 to 30 wt. % preferably 2 to 20 wt. %

Wettable Powder

Active ingredient: 2.5 to 90 wt. % preferably 10 to 80 wt. % especially 20 to 75 wt. %

Surfactant: 0.5 to 20 wt. % preferably 1 to 15 wt. % especially 2 to 10 wt. %

Solid carrier: 5 to 90 wt. % preferably 7.5 to 88 wt. % especially 16 to 56 wt. %

Granule

Active ingredient: 0. 5 to 30 wt. %

Solid carrier: 99.5 to 70 wt. %

The emulsifiable concentrate is prepared by dissolving the active ingredient in the liquid carrier with the surfactant. The wettable powder is prepared by admixing the active ingredient with the solid carrier and the surfactant and the mixture is pulverized.

The flowable suspension is prepared by suspending to disperse a pulverized active ingredient into an aqueous solution of a surfactant. The dust, the solution, the granule etc. are prepared by mixing the active ingredient with the adjuvant.

In the following compositions, the following adjuvants are used.

| Sorpol-2680 | |
|---|---|
| POE- hormylnonylphenolether | 50 wt.parts |
| POE-nonylphenolether | 20 wt.parts |
| POE-sorbitan alkyl ester | 10 wt.parts |
| Ca-alkylbenzenesulfonate | 20 wt.parts |
| Sorpol-5039 | |
| POE- alkylarylether sulfate | 50 wt.parts |
| Silica hydrate | 50 wt.parts |
| Carplex | |
| Silica hydrate | 100 wt.parts |
| Zeeklite | |
| Clay | 100 wt.parts |
| Sorpol W-150 | |
| POE-nonylphenolether | 100 wt.parts |

| Composition 1: Wettable powder: | |
|---|---|
| Active ingredient | 50 wt.parts |
| Zeeklite A | 46 wt.parts |
| Sorpol 5039 (Toho Chem.) | 2 wt.parts |
| Carplex | 2 wt.parts |

These components were uniformly mixed and pulverized to prepare a wettable powder. The wettable powder was diluted with water at 50 to 1,000 times and the diluted solution was sprayed at a dose of 5 to 1,000 g. of the active ingredient per 10 ares.

| Composition 2: Emulsifiable concentrate: | |
|---|---|
| Active ingredient | 20 wt.parts |
| Xylene | 75 wt.parts |
| Sorpol 2680 (Toho Chem.) | 5 wt.parts |

The components were uniformly mixed to prepare an emulsifiable concentrate. The emulsifiable concentrate was diluted with water at 50 to 1,000 times and the diluted solution was sprayed at a dose of 5 to 1000 g. of the active ingredient per 10 ares.

| Composition 4: Wettable powder: | |
|---|---|
| Active ingredient | 30 wt.parts |
| Other herbicide | 20 wt.parts |
| Zeeklite A | 46 wt.parts |
| Sorpol 5039 (Toho Chem.) | 2 wt.parts |
| Carplex | 2 wt.parts |

As the other herbicide, the following known herbicides were respectively used 2-(2,4-dichlorophenoxy)propionic acid, 2,4- dichlorophenoxyacetic acid, 3-(3-trifluoromethylphenyl)-1,1-dimethylurea, 3-(4-methylphenethyloxyphenyl)-1-methyl-1-methoxy urea, 3-(methoxycarbonylamino)-phenyl-N-(3-methylphenyl) carbamate, 3-(ethoxycarbonylamino)-phenyl-N-phenylcarbamate, 3-isopropyl-1H-2,1,3-benzo thiadiazine-(4)-3H- one-2,2-dioxide, 5-amino-4-chloro-2-phenylpyridazine-3-one, 3-cyclohexyl-5,6-trimethyleneuracil, 2-chloro-4-ethylamino-6-isopropylamino-1,3,5-triazine, 2-chloro-4,6-di(ethylamino)-1,3,5-triazine, 2-methylthio-4,6-bis(isopropylamino)-1,3,5-triazine, 4-amino-4,5-dihydro-3-methyl-6-phenyl-1,2,4-triazine-5-one, 4-amino-6-t-butyl-4,5-dihydro-3-methylthio-1,2,4-triazine-5-one, 2-chloro-4-trifluoromethylphenyl-3'-ethoxy-4'-nitrophenyl ether or sodium-5-2-chloro-4-(trifluoromethyl)phenoxy-2-nitro benzoate.

It is also possible to combine the compound of the present invention with the other herbicidal compounds which are described in "Weed Control Handbook" (Vol. I 6th edition 1977; Vol. II 8th edition 1978 ) issued by the British Crop Protection Council edited by J. D. Fryer M A & R. J. Makepeace BSc . Blackwell Scientific Publication.

The quinoxaline derivatives of the present invention impart excellent herbicidal effect to various weeds especially gramineous weeds in a soil treatment or in a foliage treatment, without any phytotoxicity to broad leaf crop plants such as cotton, soybean, radish, cabbage, eggplant, tomato, sugar beet, ground nut, peas, beans, line seed, sun flower, safflower, potato, tabacco, alfalfa, onion etc. Therefore, the quinoxaline derivatives of the present invention are suitable for selective control of gramineous weeds in a culture of a broad leaf crop plant as herbicide for an agricultural and horticultural field especially up-land.

The quinoxaline derivatives of the present invention are also effective as herbicides for controlling various weeds in the agricultural and horticultural fields such as up-land, paddy field and orchard as well as non-culturated lands such as playground, vacant land, and railway sides, etc..

The herbicidal composition is usually contains 0.5 to 95 wt. % of the compound of the present invention as the active ingredient and the remainder of the adjuvants in the concentrated form. The dose of the compound of the present invention is depending upon a weather condition, a soil condition, a form of a composition, a season of an application and a kind of a crop plant and kinds of weeds and it is usually in a range of 1 to 5000 g. preferably 5 to 1000 g. of the compound of the invention per 10 ares.

The herbicidal activities of the quinoxaline derivatives of the present invention will be illustrated in the following tests.

In the following tests, the herbicidal effects of the compounds of the present invention to gramineous weeds including rice are shown together with non-phytotoxicity of the same compounds to broad leaf crop plants as well as broad leaf weeds especially, non-phytotoxicity of the same compounds to broad leaf weeds in post-emergence. These remarkable selectivities have not been found by the other compounds.

Test 1: Tests for Herbicidal Effect in Soil Treatment

Each plastic box having a length of 15 cm, a width of 22 cm and a depth of 6 cm was filled with a sterilized diluvium soil and seeds of rice (*Oryza sativa*), barnyard grass (*Echinochloa crus-galli*), large crab-grass (*Digitaria adscendens*), lambsquarters (*Chenopodium ficifolium*), common purslane (*Postuloca oleracea*), hairy galinsoga (*Galinsoga ciliata*), yellow cress (*Rorippa atrovirens*) were sown in a depth of about 1.5 cm. Each solution of each herbicidal composition was uniformly sprayed on the surface of the soil to give the specific dose of the active ingredient.

The solution was prepared by diluting, with water, a wettable powder, an emulsifiable concentrate or a solution described in examples of the composition except varying the active ingredient. The solution was sprayed by a small spray. Three weeks after the treatment, the herbicidal effects to rice and various weeds were observed and rated by the following standard. The results are shown in Table 2.

Standard Rating

5: Growth control of more than 90% (substantial suppression)
4: Growth control of 70 to 90%
3: Growth control of 40 to 70%
2: Growth control of 20 to 40%
1: Growth control of 5 to 20%
0: Growth control of less than 5% (non-herbicidal effect)

Note:
Ri: Rice
Ba.: Barnyard grass
L.C.: Large crab grass
La.: Lambsquarters
C.P.: Common purslane
H.G.: Hairy galinsoga
Y.C.: Yellow cress

TABLE 2

| Comp. No. | Dose of Comp. (g/a) | Ri | Ba | L.C. | La. | C.P. | H.G. | Y.C. |
|---|---|---|---|---|---|---|---|---|
| 1 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 2 | 100 | 5 | 5 | 5 | 3 | 3 | 3 | 3 |
|  | 50 | 5 | 5 | 5 | 2 | 1 | 1 | 2 |
|  | 25 | 5 | 5 | 5 | 0 | 0 | 0 | 0 |
| 3 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 4 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 5 | 100 | 5 | 5 | 5 | 2 | 2 | 2 | 2 |
|  | 50 | 5 | 5 | 5 | 0 | 1 | 1 | 1 |
|  | 25 | 5 | 5 | 5 | 0 | 0 | 0 | 0 |
| 6 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 7 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 8 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 9 | 100 | 5 | 5 | 5 | 3 | 2 | 2 | 1 |
|  | 50 | 5 | 5 | 5 | 2 | 1 | 1 | 0 |
|  | 25 | 5 | 5 | 5 | 0 | 0 | 0 | 0 |
| 10 | 100 | 5 | 5 | 5 | 1 | 2 | 1 | 2 |
|  | 50 | 5 | 5 | 5 | 0 | 1 | 0 | 1 |
|  | 25 | 5 | 5 | 5 | 0 | 0 | 0 | 0 |
| 11 | 100 | 5 | 5 | 5 | 2 | 3 | 2 | 2 |
|  | 50 | 5 | 5 | 5 | 1 | 2 | 1 | 1 |
|  | 25 | 5 | 5 | 5 | 0 | 0 | 0 | 0 |
| 12 | 100 | 5 | 5 | 5 | 2 | 1 | 2 | 2 |
|  | 50 | 5 | 5 | 5 | 1 | 0 | 1 | 1 |
|  | 25 | 5 | 5 | 5 | 0 | 0 | 0 | 0 |
| 13 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 14 | 100 | 5 | 5 | 5 | 1 | 2 | 2 | 2 |
|  | 50 | 5 | 5 | 5 | 0 | 1 | 1 | 1 |
|  | 25 | 5 | 5 | 5 | 0 | 0 | 0 | 0 |
| 15 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 16 | 100 | 5 | 5 | 5 | 2 | 1 | 2 | 2 |
|  | 50 | 5 | 5 | 5 | 0 | 0 | 1 | 1 |
|  | 25 | 5 | 5 | 5 | 0 | 0 | 0 | 0 |
| 17 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 18 | 100 | 5 | 5 | 5 | 2 | 3 | 2 | 2 |
|  | 50 | 5 | 5 | 5 | 1 | 2 | 1 | 0 |
|  | 25 | 5 | 5 | 5 | 0 | 0 | 0 | 0 |
| 19 | 100 | 5 | 5 | 5 | 1 | 2 | 3 | 2 |
|  | 50 | 5 | 5 | 5 | 0 | 1 | 2 | 1 |
|  | 25 | 5 | 5 | 5 | 0 | 0 | 0 | 0 |
| 20 | 100 | 5 | 5 | 5 | 2 | 1 | 2 | 2 |
|  | 50 | 5 | 5 | 5 | 1 | 0 | 1 | 1 |
|  | 25 | 5 | 5 | 5 | 0 | 0 | 0 | 0 |
| 21 | 100 | 5 | 5 | 5 | 2 | 2 | 1 | 2 |
|  | 50 | 5 | 5 | 5 | 1 | 1 | 0 | 1 |
|  | 25 | 5 | 5 | 5 | 0 | 0 | 0 | 0 |
| 22 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 23 | 100 | 5 | 5 | 5 | 2 | 1 | 2 | 2 |
|  | 50 | 5 | 5 | 5 | 1 | 0 | 1 | 1 |
|  | 25 | 5 | 5 | 5 | 0 | 0 | 0 | 0 |
| 24 | 100 | 5 | 5 | 5 | 2 | 2 | 2 | 3 |
|  | 50 | 5 | 5 | 5 | 1 | 1 | 1 | 2 |
|  | 25 | 5 | 5 | 5 | 0 | 0 | 0 | 0 |
| 25 | 100 | 5 | 5 | 5 | 1 | 2 | 2 | 2 |
|  | 50 | 5 | 5 | 5 | 0 | 1 | 1 | 1 |
|  | 25 | 5 | 5 | 5 | 0 | 0 | 0 | 0 |
| 26 | 100 | 5 | 5 | 5 | 1 | 2 | 2 | 2 |
|  | 50 | 5 | 5 | 5 | 0 | 1 | 1 | 1 |
|  | 25 | 5 | 5 | 5 | 0 | 0 | 0 | 0 |
| 27 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 28 | 100 | 5 | 5 | 5 | 3 | 2 | 1 | 2 |
|  | 50 | 5 | 5 | 5 | 2 | 1 | 0 | 1 |
|  | 25 | 5 | 5 | 5 | 0 | 0 | 0 | 0 |
| 29 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |

Test 2: Tests for Herbicidal Effect in Foliage Treatment

Each plastic box having a length of 15 cm, a width of 22 cm, a depth of 6 cm was filled with a sterilized diluvium soil and seeds of rice, barnyard grass, large crab-grass, lambsquarters common purslane, hairy galinsoga, yellow cress and tomato were sown in a form of spots in a depth of about 1.5 cm. When the weeds were grown to 2 to 3 leaf stage, each solution of each herbicidal composition was uniformly sprayed to foliages at each dose of each active ingredient shown in Table 3. The solution was prepared by diluting, with water, a wettable powder, an emulsifiable concentrate or a solution described in examples of the composition except varying the active ingredient and the solution was uniformly sprayed by a small spray on all of foliages of the plants.

Two weeks after the spray treatment, the herbicidal effects to the weeds and tomato were observed and rated by the standard shown in Test 1. The results are shown in Table 3.

TABLE 3

| Comp. No. | Dose of Comp. (g/a) | Ri | Ba | L.C. | La. | C.P. | H.G. | Y.C. |
|---|---|---|---|---|---|---|---|---|
| 1 | 100 | 5 | 5 | 5 | 2 | 2 | 2 | 3 |
|  | 50 | 5 | 5 | 5 | 1 | 1 | 0 | 2 |
|  | 25 | 5 | 5 | 5 | 0 | 0 | 0 | 0 |

TABLE 3-continued

| Comp. No. | Dose of Comp. (g/a) | Ri | Ba | L.C. | La. | C.P. | H.G. | Y.C. |
|---|---|---|---|---|---|---|---|---|
| 2 | 100 | 5 | 5 | 5 | 3 | 2 | 2 | 2 |
|  | 50 | 5 | 5 | 5 | 1 | 1 | 1 | 1 |
|  | 25 | 5 | 5 | 5 | 0 | 0 | 0 | 0 |
| 3 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 4 | 100 | 5 | 5 | 5 | 1 | 1 | 1 | 1 |
|  | 50 | 5 | 5 | 5 | 0 | 0 | 0 | 0 |
|  | 25 | 5 | 5 | 5 | 0 | 0 | 0 | 0 |
| 5 | 100 | 5 | 5 | 5 | 2 | 3 | 2 | 2 |
|  | 50 | 5 | 5 | 5 | 1 | 2 | 1 | 1 |
|  | 25 | 5 | 5 | 5 | 0 | 0 | 0 | 0 |
| 6 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 7 | 100 | 5 | 5 | 5 | 2 | 1 | 1 | 2 |
|  | 50 | 5 | 5 | 5 | 1 | 1 | 0 | 1 |
|  | 25 | 5 | 5 | 5 | 0 | 0 | 0 | 0 |
| 8 | 100 | 5 | 5 | 5 | 2 | 1 | 1 | 1 |
|  | 50 | 5 | 5 | 5 | 1 | 0 | 0 | 1 |
|  | 25 | 5 | 5 | 5 | 0 | 0 | 0 | 0 |
| 9 | 100 | 5 | 5 | 5 | 2 | 2 | 1 | 2 |
|  | 50 | 5 | 5 | 5 | 0 | 1 | 0 | 1 |
|  | 25 | 5 | 5 | 5 | 0 | 0 | 0 | 0 |
| 10 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 11 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 12 | 100 | 5 | 5 | 5 | 2 | 3 | 2 | 2 |
|  | 50 | 5 | 5 | 5 | 1 | 2 | 1 | 1 |
|  | 25 | 5 | 5 | 5 | 0 | 0 | 0 | 0 |
| 13 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 14 | 100 | 5 | 5 | 5 | 3 | 2 | 1 | 2 |
|  | 50 | 5 | 5 | 5 | 1 | 1 | 0 | 1 |
|  | 25 | 5 | 5 | 5 | 0 | 0 | 0 | 0 |
| 15 | 100 | 5 | 5 | 5 | 1 | 1 | 1 | 1 |
|  | 50 | 5 | 5 | 5 | 0 | 0 | 0 | 0 |
|  | 25 | 5 | 5 | 5 | 0 | 0 | 0 | 0 |
| 16 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 17 | 100 | 5 | 5 | 5 | 1 | 1 | 1 | 1 |
|  | 50 | 5 | 5 | 5 | 0 | 0 | 0 | 0 |
|  | 25 | 5 | 5 | 5 | 0 | 0 | 0 | 0 |
| 18 | 100 | 5 | 5 | 5 | 2 | 2 | 2 | 3 |
|  | 50 | 5 | 5 | 5 | 1 | 1 | 1 | 2 |
|  | 25 | 5 | 5 | 5 | 0 | 0 | 0 | 0 |
| 19 | 100 | 5 | 5 | 5 | 1 | 2 | 2 | 2 |
|  | 50 | 5 | 5 | 5 | 0 | 1 | 1 | 1 |
|  | 25 | 5 | 5 | 5 | 0 | 0 | 0 | 0 |
| 20 | 100 | 5 | 5 | 5 | 2 | 2 | 2 | 2 |
|  | 50 | 5 | 5 | 5 | 1 | 1 | 0 | 1 |
|  | 25 | 5 | 5 | 5 | 0 | 0 | 0 | 0 |
| 21 | 100 | 5 | 5 | 5 | 2 | 1 | 2 | 2 |
|  | 50 | 5 | 5 | 5 | 1 | 0 | 0 | 1 |
|  | 25 | 5 | 5 | 5 | 0 | 0 | 0 | 0 |
| 22 | 100 | 5 | 5 | 5 | 2 | 1 | 1 | 1 |
|  | 50 | 5 | 5 | 5 | 1 | 0 | 0 | 0 |
|  | 25 | 5 | 5 | 5 | 0 | 0 | 0 | 0 |
| 23 | 100 | 5 | 5 | 5 | 2 | 3 | 2 | 2 |
|  | 50 | 5 | 5 | 5 | 1 | 2 | 1 | 1 |
|  | 25 | 5 | 5 | 5 | 0 | 0 | 0 | 0 |
| 24 | 100 | 5 | 5 | 5 | 2 | 2 | 2 | 1 |
|  | 50 | 5 | 5 | 5 | 1 | 1 | 1 | 0 |
|  | 25 | 5 | 5 | 5 | 0 | 0 | 0 | 0 |
| 25 | 100 | 5 | 5 | 5 | 2 | 2 | 2 | 2 |
|  | 50 | 5 | 5 | 5 | 1 | 1 | 1 | 1 |
|  | 25 | 5 | 5 | 5 | 0 | 0 | 0 | 0 |
| 26 | 100 | 5 | 5 | 5 | 3 | 2 | 2 | 2 |
|  | 50 | 5 | 5 | 5 | 2 | 1 | 1 | 1 |
|  | 25 | 5 | 5 | 5 | 0 | 0 | 0 | 0 |
| 27 | 100 | 5 | 5 | 5 | 2 | 2 | 2 | 1 |
|  | 50 | 5 | 5 | 5 | 1 | 1 | 1 | 0 |
|  | 25 | 5 | 5 | 5 | 0 | 0 | 0 | 0 |
| 28 | 100 | 5 | 5 | 5 | 1 | 1 | 1 | 2 |
|  | 50 | 5 | 5 | 5 | 0 | 0 | 0 | 1 |
|  | 25 | 5 | 5 | 5 | 0 | 0 | 0 | 0 |
| 29 | 100 | 5 | 5 | 5 | 2 | 2 | 2 | 1 |
|  | 50 | 5 | 5 | 5 | 1 | 1 | 1 | 0 |
|  | 25 | 5 | 5 | 5 | 0 | 0 | 0 | 0 |

Test 3: Tests for Phytotoxicity to Crop Plants (Foliage Treatment)

Each plastic box having a length of 15 cm, a width of 22 cm, and a depth of 6 cm was filled with a sterilized diluvium soil and seeds of cotton, soybean, radish, cabbage and eggplant were sown in a form of spots in a depth of about 1.5 cm. When the plants were grown to leaf-emergence stage, each solution of each herbicidal composition was uniformly sprayed to foliages at each dose of each active ingredient shown in Table 4. The solution was prepared by diluting, with water, a wettable powder, an emulsifiable concentrate or a solution described in examples of the composition except varying the active ingredient and the solution was uniformly sprayed by a small spray on all of foliages of the plants.

Two weeks after the spray treatment, the phytotoxicities to the plants were observed and rated by the following standard. The results are shown in Table 4.

Standard Rating

5: Complete death of plant

4: Serious phytotoxicity to plant

3: Fair phytotoxicity to plant

2: Slight phytotoxicity to plant

1: Only slight phytotoxicity to plant

0: Non phytotoxicity

Note:

Cot.: Cotton

Soy.: Soybean

Rad.: Radish

Cab.: Cabbage

Egg.: Eggplant

TABLE 4

| Compound No. | Dose of Compound (g/a) | Cot. | Soy. | Rad. | Cab. | Egg. |
|---|---|---|---|---|---|---|
| 1 | 50 | 0 | 0 | 0 | 0 | 0 |
|  | 25 | 0 | 0 | 0 | 0 | 0 |
| 2 | 50 | 0 | 0 | 0 | 0 | 0 |
|  | 25 | 0 | 0 | 0 | 0 | 0 |

TABLE 4-continued

| Compound No. | Dose of Compound (g/a) | Cot. | Soy. | Rad. | Cab. | Egg. |
|---|---|---|---|---|---|---|
| 3 | 50 | 0 | 0 | 0 | 0 | 0 |
|   | 25 | 0 | 0 | 0 | 0 | 0 |
| 4 | 50 | 0 | 0 | 0 | 0 | 0 |
|   | 25 | 0 | 0 | 0 | 0 | 0 |
| 5 | 50 | 0 | 0 | 0 | 0 | 0 |
|   | 25 | 0 | 0 | 0 | 0 | 0 |
| 6 | 50 | 0 | 0 | 0 | 0 | 0 |
|   | 25 | 0 | 0 | 0 | 0 | 0 |
| 7 | 50 | 0 | 0 | 0 | 0 | 0 |
|   | 25 | 0 | 0 | 0 | 0 | 0 |
| 8 | 50 | 0 | 0 | 0 | 0 | 0 |
|   | 25 | 0 | 0 | 0 | 0 | 0 |
| 9 | 50 | 0 | 0 | 0 | 0 | 0 |
|   | 25 | 0 | 0 | 0 | 0 | 0 |
| 10 | 50 | 0 | 0 | 0 | 0 | 0 |
|    | 25 | 0 | 0 | 0 | 0 | 0 |
| 11 | 50 | 0 | 0 | 0 | 0 | 0 |
|    | 25 | 0 | 0 | 0 | 0 | 0 |
| 12 | 50 | 0 | 0 | 0 | 0 | 0 |
|    | 25 | 0 | 0 | 0 | 0 | 0 |
| 13 | 50 | 0 | 0 | 0 | 0 | 0 |
|    | 25 | 0 | 0 | 0 | 0 | 0 |
| 14 | 50 | 0 | 0 | 0 | 0 | 0 |
|    | 25 | 0 | 0 | 0 | 0 | 0 |
| 15 | 50 | 0 | 0 | 0 | 0 | 0 |
|    | 25 | 0 | 0 | 0 | 0 | 0 |
| 16 | 50 | 0 | 0 | 0 | 0 | 0 |
|    | 25 | 0 | 0 | 0 | 0 | 0 |
| 17 | 50 | 0 | 0 | 0 | 0 | 0 |
|    | 25 | 0 | 0 | 0 | 0 | 0 |
| 18 | 50 | 0 | 0 | 0 | 0 | 0 |
|    | 25 | 0 | 0 | 0 | 0 | 0 |
| 19 | 50 | 0 | 0 | 0 | 0 | 0 |
|    | 25 | 0 | 0 | 0 | 0 | 0 |
| 20 | 50 | 0 | 0 | 0 | 0 | 0 |
|    | 25 | 0 | 0 | 0 | 0 | 0 |
| 21 | 50 | 0 | 0 | 0 | 0 | 0 |
|    | 25 | 0 | 0 | 0 | 0 | 0 |
| 22 | 50 | 0 | 0 | 0 | 0 | 0 |
|    | 25 | 0 | 0 | 0 | 0 | 0 |
| 23 | 50 | 0 | 0 | 0 | 0 | 0 |
|    | 25 | 0 | 0 | 0 | 0 | 0 |
| 24 | 50 | 0 | 0 | 0 | 0 | 0 |
|    | 25 | 0 | 0 | 0 | 0 | 0 |
| 25 | 50 | 0 | 0 | 0 | 0 | 0 |
|    | 25 | 0 | 0 | 0 | 0 | 0 |
| 26 | 50 | 0 | 0 | 0 | 0 | 0 |
|    | 25 | 0 | 0 | 0 | 0 | 0 |
| 27 | 50 | 0 | 0 | 0 | 0 | 0 |
|    | 25 | 0 | 0 | 0 | 0 | 0 |
| 28 | 50 | 0 | 0 | 0 | 0 | 0 |
|    | 25 | 0 | 0 | 0 | 0 | 0 |
| 29 | 50 | 0 | 0 | 0 | 0 | 0 |
|    | 25 | 0 | 0 | 0 | 0 | 0 |

What is claimed is:

1. A method of controlling unwanted plant growth which comprises treating the unwanted plants or the locus thereof with a herbicidally effective amount of a compound of the formula (I):

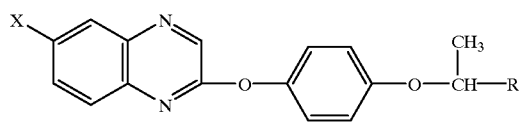

wherein X represents a halogen atom; R represents —COR$^1$,

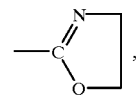

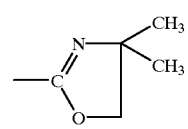

or —CH$_2$OH, and R$^1$ represents

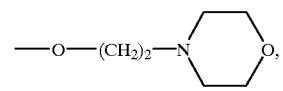

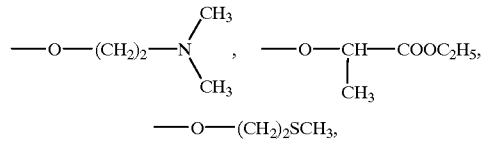

—O—(CH$_2$)$_2$SCH$_3$,

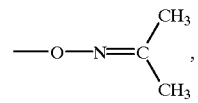

—S—R$^3$ (R$^3$ represents a C$_1$–C$_4$ alkyl or alkenyl group or phenyl or chlorophenyl group) or —NH—R$^4$ (R$^4$ represents a C$_1$–C$_4$ alkoxy carbonylalkyl group, hydroxy alkyl group, C$_1$–C$_4$ alkoxy alkyl group or di C$_1$–C$_4$ alkyl amino group).

2. A method according to claim 1 wherein X is chlorine.

3. A method according to claim 1 wherein X is fluorine.

4. A method according to claim 1 for the selective control of monocot weeds in crops of cultivated plants.

5. A method according to claim 1 for the selective control of gramineous plants in crops of cultivated broad leaf plants.

6. A method according to claim 1 wherein the compound is applied post-emergence.

7. A method of influencing plant growth which comprises treating the plants to be influenced with a herbicidally effective amount of a compound of the formula (I):

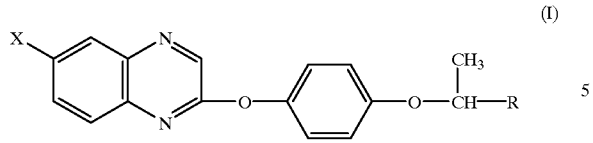 (I)
wherein X represents a halogen atom; R represents —COR¹,
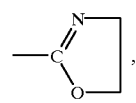,
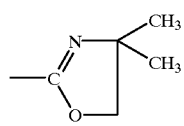
or —CH$_2$OH, and R¹ represents
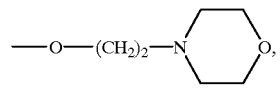,
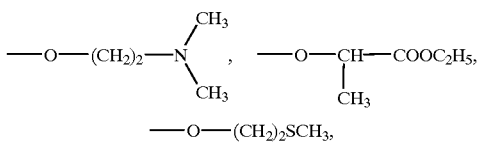
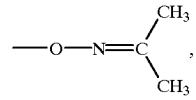,
—S—R³ (R³ represents a C$_1$–C$_4$ alkyl or alkenyl group or phenyl or chlorophenyl group) or —NH—R⁴ (R⁴ represents a C$_1$–C$_4$ alkoxy carbonylalkyl group, hydroxy alkyl group, C$_1$–C$_4$ alkoxy alkyl group or di C$_1$–C$_4$ alkyl amino group).
\* \* \* \* \*